United States Patent [19]

Ryan

[11] Patent Number: 4,923,445
[45] Date of Patent: May 8, 1990

[54] SAFETY NEEDLED MEDICAL DEVICES

[75] Inventor: Dana W. Ryan, Brentwood, Tenn.

[73] Assignee: Ryan Medical, Inc., Brentwood, Tenn.

[21] Appl. No.: 224,920

[22] Filed: Jul. 27, 1988

Related U.S. Application Data

[63] Continuation-in-part of Ser. No. 162,569, Mar. 1, 1988.

[51] Int. Cl.$^5$ ............................................. A61M 5/32
[52] U.S. Cl. ..................................... 604/195; 604/198
[58] Field of Search ............... 604/198, 263, 192, 187, 604/195

[56] References Cited

U.S. PATENT DOCUMENTS

| | | | |
|---|---|---|---|
| 3,890,971 | 6/1975 | Leeson et al. | 604/198 X |
| 4,655,751 | 4/1987 | Harbaugh | 604/198 |
| 4,702,738 | 10/1987 | Spencer | 604/198 |
| 4,737,144 | 4/1988 | Choksl | 604/198 |
| 4,758,231 | 7/1988 | Haber et al. | 604/198 |
| 4,790,827 | 12/1988 | Haber et al. | 604/198 |
| 4,816,022 | 3/1989 | Poncy | 604/198 |

Primary Examiner—John D. Yasko
Attorney, Agent, or Firm—David P. Gordon

[57] ABSTRACT

Improved shielded medical devices which minimize accidental needlesticks of the skin by an exposed contaminated needle are provided. The medical devices include a hollow inner tube body having at least two circumferential grooves on the outside thereof, and a slightly larger diameter hollow shield which is slidable relative to the inner tube. A first circumferential protrusion which is located at the rearward end of the shield yieldingly engages the rearward groove during use of the medical device and thereby permits normal use of an exposed needle. Thereafter the shield may be moved along the longitudinal axis of the inner tube to a second position where the shield covers the now-contaminated needle. In the shielded second position a second circumferential protrusion which is located in forward proximity to the first protrusion engages the forward groove of the inner tube. The first protrusion meanwhile engages the outer surface of the inner tube and provides additional stability and strength against axial and torque forces. The inner tube has a shoulder located forward of the forward groove to help prevent the second circumferential protrusion of the shield from disengaging from the forward groove.

23 Claims, 5 Drawing Sheets

U.S. Patent  May 8, 1990  Sheet 1 of 5  4,923,445
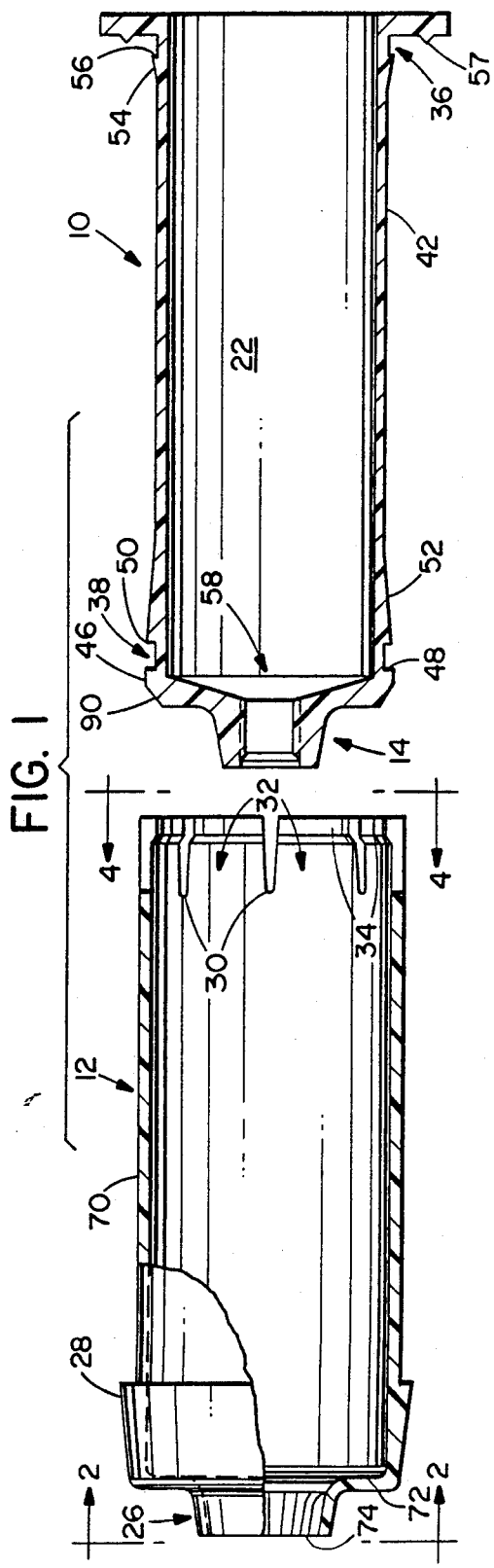
FIG. 1
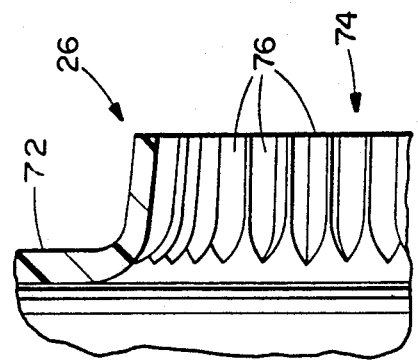
FIG. 3
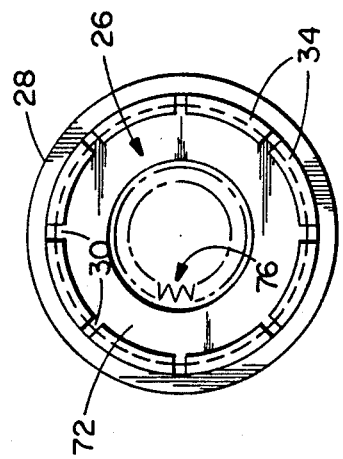
FIG. 4
FIG. 2

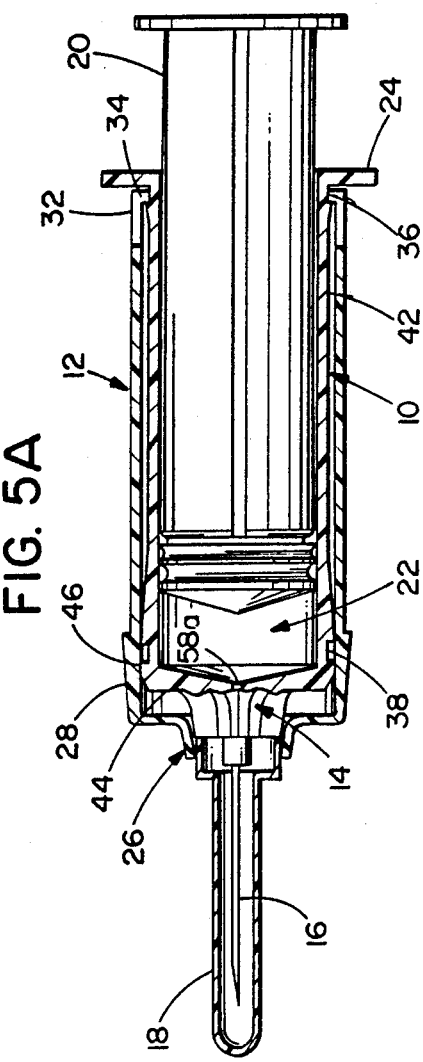
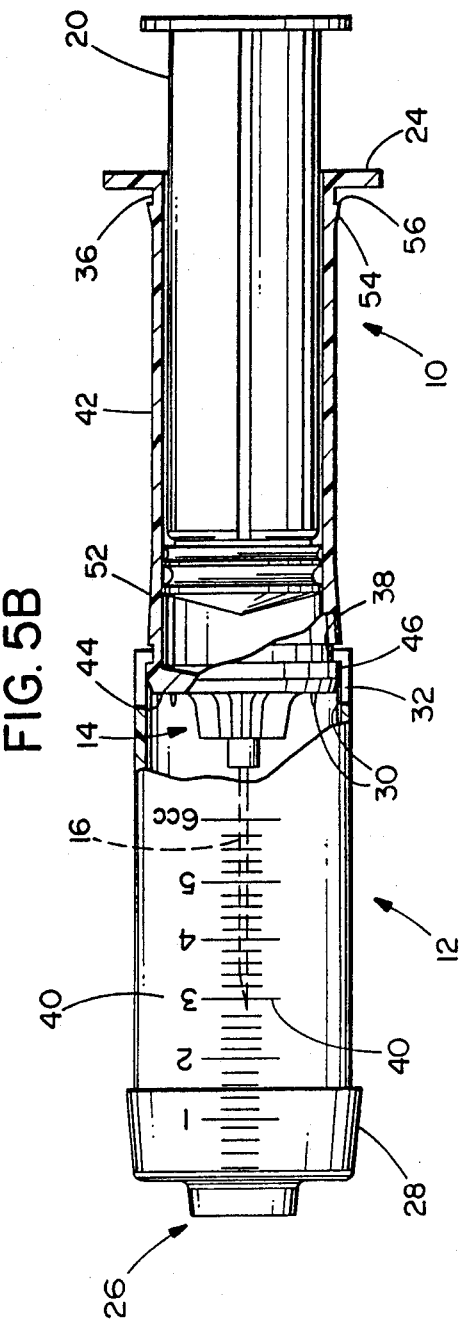
FIG. 5A
FIG. 5B

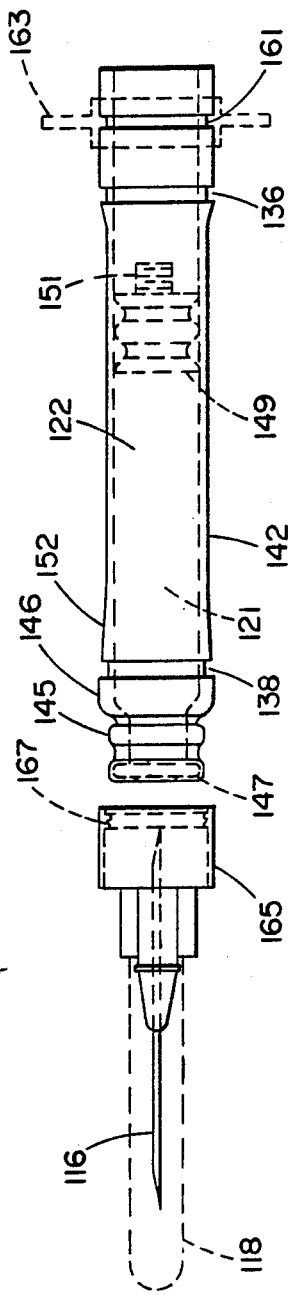
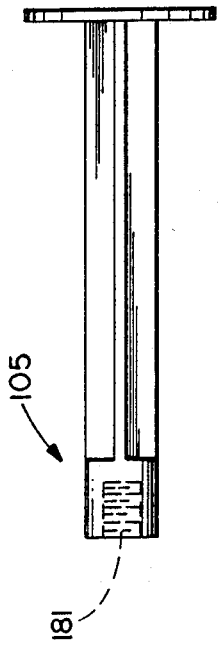
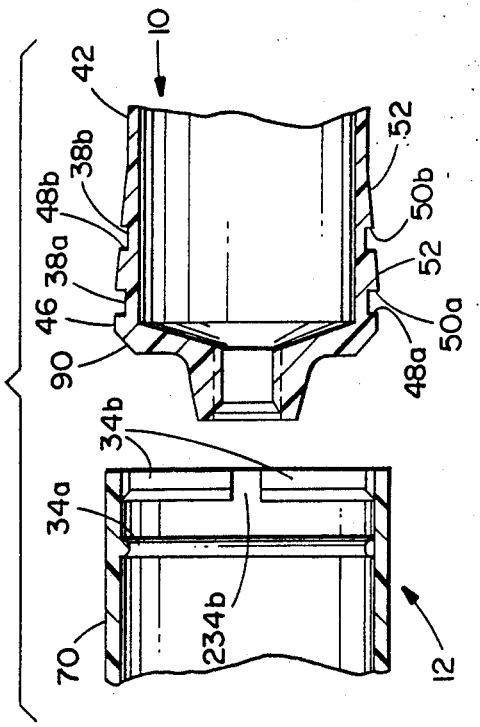

SAFETY NEEDLED MEDICAL DEVICES

A continuation-in-part of Ser. No. 162,569 filed Mar. 1, 1988, and which is hereby incorporated by reference herein.

BACKGROUND OF THE INVENTION

The present invention generally relates to improvements in safety needled medical devices which are designed to minimize the incidence of accidental pricking of the skin and resulting spread of infectious diseases by an exposed contaminated needle after use thereof. The disclosed devices may be used as blood collection tube holders, syringes with or without an attached needle, and prefilled syringes.

Accidental needlesticks have long been a problem in the medical profession. Accidental needlesticks most often occur during the recapping of a contaminated needle or immediately after use and prior to safe disposal. Such needlesticks place the medical professional (clinician) at risk. When needles are not recapped, additional accidental needlesticks are caused by uncapped needles found in patient beds, linens, and in garbage cans, and place health care housekeeping and sanitation personnel at risk. Because accidental needlesticks can now result in deadly incurable diseases as well as the previously appreciated serious, but curable diseases, the need for eliminating the needlestick problem has reached extreme urgency. In addressing the urgency, many devices have been proposed. Indeed, the prior art discloses a number of devices which are arranged to shield the needle of the device after use, but none are as simple to manufacture, assemble, and use as the devices of the present invention. A benefit of the devices of the present invention is that the devices require no change in the method of use or technique by medical personnel, i.e., the medical practioners will use the devices in the same way they previously used standard hypodermic syringes, IV catheters, and blood collection tube holders, except that after use they will move a shield to cover the exposed contaminated needle in a very easy, simple and straightforward manner.

Included in the prior art among many safety devices are safety-needled syringes such as are disclosed in U.S. Pat Nos. 2,571,653 to Bastien, 4,026,287 to Haller, 4,425,120 to Sampson et al., 4,573,976 to Sampson et al., 4,631,057 to Mitchell, 4,643,199 to Jennings, Jr. et al., 4,655,751 to Harbaugh, 4,666,435 to Braginetz, 4,681,567 to Masters et al. None of these devices, however, have gained acceptance due to the fact that they require many complex pieces and thus become expensive to manufacture and assemble, and/or because in utilizing the devices, they require the clinician's procedure and technique to change. For example, in U.S. Pat. No. 4,425,120 to Sampson et al, a complex arrangement of tracks including axial and circumferential components of shield and syringe members are required, making manufacture and assembly more difficult and expensive. Also, in use, the clinician must rotate the shield relative to the syringe tube and force the track engaging member of the syringe through a restriction in the circumferential portion of the track in the shield to lock the shield relative to the syringe tube. The U.S. Pat. No. 4,631,057 to Mitchell requires a collar member over which a shield slides. The device is complex, difficult to manufacture and assemble, and requires permanent attachment of the collar to the syringe tube. The U.S. Pat. No. 4,573,976 to Sampson et al., requires additional intricate members which are attached to both the tube and the shield and which provide a locking action. The additional members are expensive to manufacture and assemble, unwieldy to handle, and would require a clinician to develop a new technique for utilization.

U.S. Pat. No. 4,655,751 to Harbaugh requires at least one slide groove to maintain the shield in the proper rotational axis and to thereby align a pair of ears on the shield with either one of two pairs of pockets in the outer surface of the syringe tube. Besides being relatively expensive to manufacture and assemble due to the ears and pockets, it also requires flexing of the shield to move it to the needle-shielding position, and thus has the potential for cracking or breaking. Similarly, U.S. Pat. No. 4,681,567 to Masters et al., requires a slide grooves in a shield and knobs or ears on the tube. Restrictions in the groove provide locking positions for the shield. Again, however, the knobs may be costly to manufacture and assemble and are prone to breaking.

U.S. Pat. No. 4,666,435 to Braginetz requires a complex and difficult to manufacture arrangement of tracks, rails, detents and stop surfaces, and would be much more expensive to make and assemble than the present invention. Further, to lock the syringe tube and shield, the user must step through a predetermined sequence of relative rotational and longitudinal movements between the shield and the syringe tube. U.S. Pat. No. 2,571,653 to Bastien is simpler in design and has a single latch secured by a tensioning device to lock the shield at fixed points on the syringe tube, but the shield would not be as secure in its position covering the needle due to the single latch, and any mishandling of the device could cause movement of the tensioning device and exposure of the needle.

Finally, U.S. Pat. Nos. 4,026,287 to Haller and 4,643,199 to Jennings, Jr. show safety devices which utilize a technique of withdrawing the needle into the tube in order to render the needle harmless. These devices, and others like these typically require additional parts and are difficult to manipulate.

SUMMARY OF THE INVENTION

It is therefore an object of the present invention to provide improved shielded medical devices which are easy and economical to manufacture and assemble, and which do not require change of technique and procedure to use.

A further object of the present invention is to provide improved shielded medical blood collection tube holders, and syringes of different kinds with standardized locking mechanisms in which movement of the shield from the unshielded position to the locked shielded position may be accomplished in an easy, uniform sliding motion.

Another object of the invention is to provide economical improved shielded medical devices utilizing a shield which provides a positive indication when locking into a shielded position.

Yet another object of the present invention is to provide improved shielded medical devices in which rotation of the shield relative to an inner tube body is prevented when the medical device is in use.

The improved safety needled medical devices of the present invention achieve the above-listed objects as hereinafter disclosed. The devices, whether for use with syringes or blood collection tube holders, are comprised of two parts. A first part is a hollow cylindrical inner tube body which is adapted to have mounted at its forward end a standard hollow needle, and to receive a standard plunger or vacuum blood collection tube through its open rearward end. The outside of the inner tube body (hereinafter referred to as the "tube", or the "inner tube") is configured with at least two axially spaced circumferential grooves with one of the grooves preferably being formed towards the rearmost end of the tube adjacent an outward extending finger positioning flange, and at least one other groove preferably being near the forward end of the tube. The second part of the safety needled devices is an outer safety shield. The outer safety shield (hereinafter referred to as the "shield", or the "outer shield") is of slightly larger diameter than the inner tube and is assembled over the tube. The outer shield is arranged to be slidable relative to the inner tube, and preferably includes two circumferential inward protrusions in relatively close proximity one to the other towards the rear end of the outer shield. The rearward of the two protrusions is arranged to engage the rear groove of the inner tube when the shield is in a non-shielding retracted position, while the forward of the two protrusions engages the forward groove of the inner tube when the shield is slid forward into shielding position. The shield then prevents accidental contact with the contaminated needle, and the rearward protrusion of the outer shield acts both to stabilize the shield relative to the inner tube so that the shield cannot be removed, and also as a second safety catch should a user manage to force the first protrusion out of the locking groove. Ratchet, or other similar means connected with the inner tube and the outer shield are provided to prevent rotation of the outer shield relative to the inner tube when the shield is in its retracted position and the needle is exposed.

A better understanding of the improved safety needle medical devices of the present invention, and additional advantages and objects of the invention will become apparent to those skilled in the art upon reference to the detailed description and accompanying drawings.

BRIEF DESCRIPTION OF DRAWINGS

FIG. 1 is a plan view showing the standardized locking mechanism of the inner tube and outer shield of parent application invention prior to assembly as a medical safety-needled device;

FIG. 2 is an end view of the outer shield of FIG. 1, taken along line 2—2 of FIG. 1, and showing a ratchet mechanism;

FIG. 3 is a side view of the ratchet mechanism of the outer shield shown in FIG. 1;

FIG. 4 is an end view of the outer shield taken along line 4—4 of FIG. 1;

FIG. 5a is a longitudinal sectional view of the syringe embodiment of the parent application safety-needled invention where the outer shield is in a retracted position relative to the inner tube so that the needle is unshielded and ready for use;

FIG. 5b is a longitudinal sectional view of the syringe embodiment of the parent application safety needled invention where the outer shield is in an extended position relative to the inner tube so that the contaminated needle is shielded;

FIG. 9a is plan view of the inner tube for the parent application prefilled syringe embodiment of the safety-needled invention;

FIG. 9b is a plan view of the plunger arm for a prefilled syringe;

FIG. 10 is a plan view of the front of the inner tube and the rear of the outer shield of the double-protrusion standardized medical safety-needled device of the invention prior to assembly;

DETAILED DESCRIPTION OF THE PREFERRED EMBODIMENTS

Figure 7:
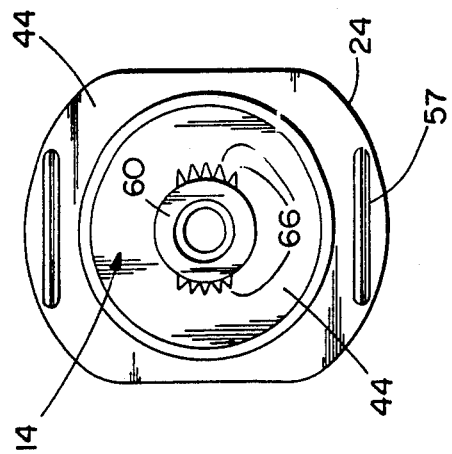
FIG. 7 is an end view of the inner tube of FIG. 6, taken along line 7—7 of FIG. 6.
Figure 6:
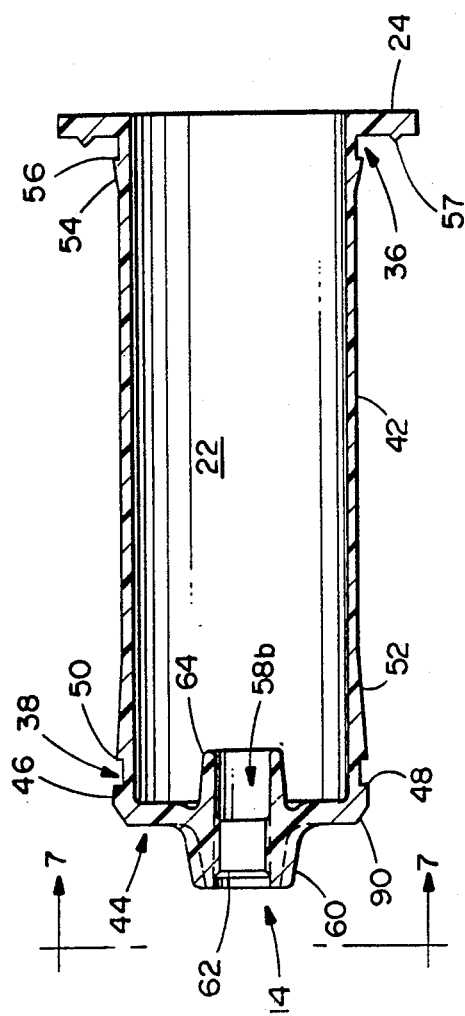
FIG. 6 is a longitudinal sectional view of the inner tube of a blood collection tube holder embodiment of the parent application invention.
Figure 8:
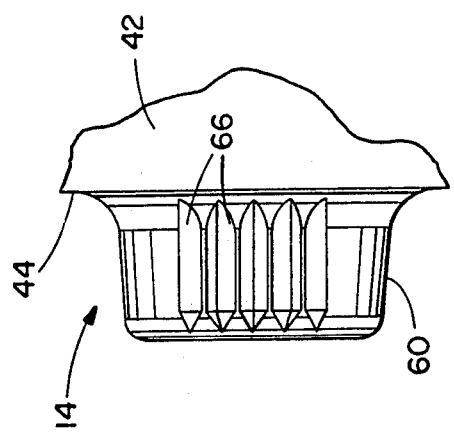
FIG. 8 is a side view of the inner tube ratchet means shown in FIG. 6.
Figure 11A:
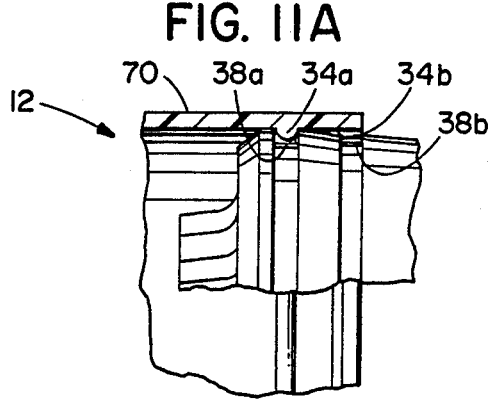
FIG. 11a is a partial longitudinal sectional view of the locking mechanisms of the double-protrusion three-groove syringe embodiment safety needled invention where the outer shield is in an extended position relative to the inner tube so that the contaminated needle is shielded.
Figure 11B:
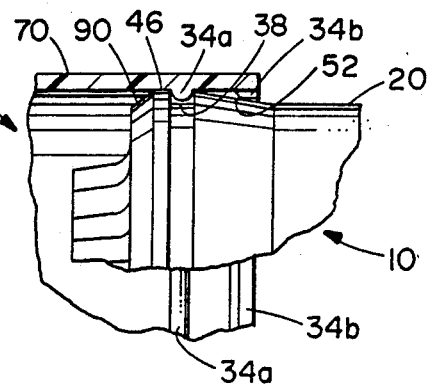
FIG. 11b is a partial longitudinal sectional view of the locking mechanisms of the double-protrusion two-groove syringe embodiment safety needled invention where the outer shield is in an extended position relative to the inner tube so that the contaminated needle is shielded.
Figure 12A:
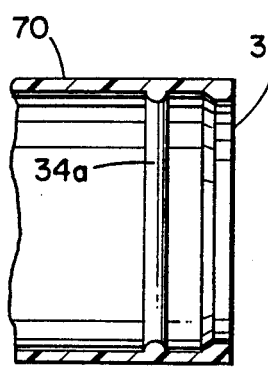
FIGS. 12a–12c are partial longitudinal sectional views of second, third and fourth embodiments of the rear of the double-protrusion outer shield, a first embodiment being seen in FIG. 10.
Figure 12B:
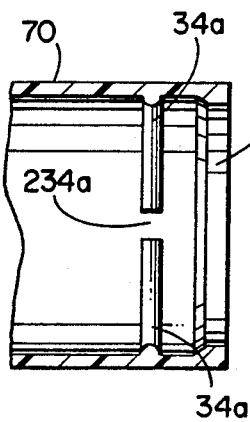
Figure 12C:
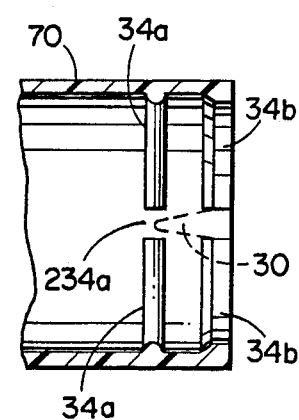
Figure 13A:
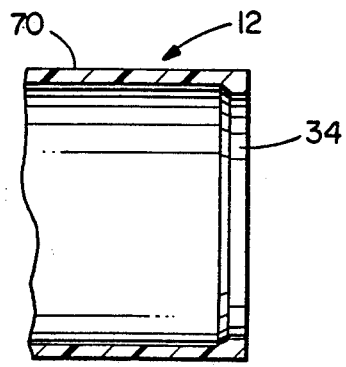
FIGS. 13a and 13b are partial longitudinal sectional views of a non-slit, single protrusion outer shield.
Figure 13B:
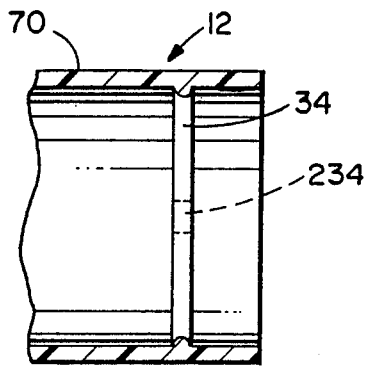

FIGS. 1–9 show the safety-needled device of the parent application with FIGS. 1–4 showing the basic structure of the safety-needled device, FIG. 5a showing the syringe embodiment with the needle exposed and ready for use, FIG. 5b showing the syringe embodiment after use with the outer shield in its forwardmost position in which the needle is covered, FIGS. 6–8 showing the blood collection tube holder embodiment, and FIG. 9 showing the prefilled syringe embodiment. FIGS. 10–12 show an improvement to the locking devices of FIGS. 1–9 where the outer shield includes two axially spaced circumferential protrusions, while FIGS. 13a and 13b show a non-slit shield having a single protrusion. FIG. 10 shows the improved locking structure with two inwardly directed protrusions on the outer shield in close proximity to each other and two forward grooves in close proximity to each other. FIGS. 11a and 11b show interlocked shields and inner tubes after use of the needle, with FIG. 11a showing two forward grooves on the inner tube and FIG. 11b showing only one forward groove on the inner tube. FIGS. 12a–12c show different embodiments of the two-protrusion arrangement of the outer shield where one or both of the protrusions may be either continuous or interrupted, and the outer shield may be slotted if desired.

Referring to FIGS. 1–4, a safety medical device comprises two generally cylindrical pieces, a hollow inner tube 10 and an outer shield 12, both pieces typically being made of molded plastic or other acceptable material. Molded into the forward end of the outer surface of inner tube 10 is a ratchet assembly 14 including locking teeth which are shown in detail in FIGS. 7 and 8 with reference to the blood collection tube holder embodiment. The inner surface of the forward end of inner tube 10 is also adapted to securely typically with a threaded structure to hold a standard hollow needle 16 shown with a removable needle cover 18 thereon. Inner tube 10 is further provided with a cavity 22 into which drugs, pharmaceuticals, blood or other fluids may be aspirated and then forced through needle 16 into a body, or into which a blood collection tube may be placed so that blood from the body may be drawn. A flange 24 is molded at the rearward end of inner tube 10 to act as a finger support while forcing the contents in the cavity into the body, or while withdrawing the needle from the patient, pharmaceutical vial, or other container.

One important aspect of the invention is the precise geometry of the outer wall 42 of the inner tube 10. Circumferential grooves 36 and 38 are formed in wall 42. An end wall 44 extends from the forwardmost end of wall 42 which is integral therewith and is described in more detail hereinafter with respect to the blood collection tube holder embodiment shown in FIGS. 6-8. At the junction of end wall 44 and wall 42 a shoulder 46 is formed, the rearward extension of shoulder 46 forming the forwardmost ledge 48 of circumferential groove 38. The rearmost ledge 50 of groove 38 has a slightly smaller diameter than that of shoulder 46, and as wall 42 extends rearward from ledge 50, its outside diameter gradually decreases to form a sloped wall portion or ramp generally illustrated by 52. Thereafter, the wall 42 is of constant diameter until it reaches slightly raised shoulder 54 which forms the forwardmost ledge 56 of circumferential groove 36. The forwardmost portion of flange 24 forms the rearwardmost ledge of groove 36, and flange 24 has tine 57 for added finger support. The advantages of the entire construction will be described hereinafter. It should be understood at this juncture, however, that the inner tube 10 is a single, preferably molded, integral unit.

The outer shield 12 has an inside diameter which is slightly larger than the outer diameter of the inner tube 10. The outer shield 12 is adapted to fit over inner tube 10 and to be slidable between a rearward position and a forward position (as respectively shown in FIGS. 5a and 5b for the syringe embodiment). The outer shield 12 has a locking nozzle or ratchet means 26 molded into its inner surface at the forward end thereof, the locking nozzle including a plurality of locking notches, shown particularly in FIGS. 2 and 3. Locking nozzle 26 is preferably annular in shape and is connected to the outer cylindrical wall 70 of shield 12 by end wall 72. A substantially annular opening 74 at the center of locking nozzle 26 is adapted to permit a standard needle 16 to extend therethrough when the shield 13 is in its closed position. As will be described, the locking nozzle 26 engages the locking teeth in the rachet assembly 14 when the shield 12 is in its rearward (retracted) position, thereby preventing rotation of the outer shield 12 relative to the inner tube 10 during an injection or phlebotomy.

A flanged safety ridge 28 is formed near the forward end of outer shield 12 to assist the user in grasping the shield 12 and slidably moving it from its retracted position to its extended and locked position. The shield 12 also has at its rearmost end a plurality of circumferentially spaced axial slots 30 which form there-between tabs 32, the tabs 32 being slightly flexible. Formed on the inner surface of tabs 32 are a plurality of protrusions or lug members 34 (seen in FIG. 4) which are adapted to yieldingly engage a circumferential groove 36 preferably located at the rear end of inner tube 10 to thereby maintain the shield 12 in its retracted position (shown in FIG. 5a with respect to the syringe embodiment). The tabs 32 are sufficiently flexible to permit the lug members 34 to be forced out of groove 36, and to permit the shield 12 to be moved forward manually to its extended or locked position (shown in FIG. 5b with respect to the syringe embodiment) in which the lug members 34 engage a second circumferential groove 38. As will be described hereinafter, the construction of the shield 12 and inner tube 10 are such that the shield 12, when in the extended locked position with lug members 34 locked into groove 38, is extremely difficult to remove from the inner tube 10, while during assembly, the shield 12 is slipped over tube 10 without lug members 34 locking into groove 38.

As aforementioned, a plurality of notches or grooves 76, shown in FIGS. 2 and 3, are formed on the inside wall of locking nozzle 26. The notches 76 are designed and sized to mesh with the raised teeth 66 extending from the outside of wall 60 of ratchet assembly 14 when shield 12 is positioned as shown in FIG. 5a with respect to the syringe embodiment. The meshing of the teeth 66 and notches 76 prevents rotation of shield 12 relative to inner tube 10 which could be distracting to the medical personnel using the medical device. While twenty-four notches 76 are shown extending completely about the inside wall of locking nozzle 26, the exact number and shape may be varied and will be dependent on the size, shape and location of raised teeth 66. With raised teeth 66 on opposite sides of wall 60, the teeth 66 will mesh with notches 76 regardless of the relative circumferential alignment between inner tube 10 and outer shield 12.

Another important feature of the invention is the plurality of forwardly extending slits 30 in the rearward portion of wall 70 of shield 12. As shown, eight such slits 30 are provided, although the exact number will depend on the size of the shield 12 and the flexibility of the plastic or other acceptable material from which it is constructed. As seen in FIGS. 1 and 4, the slits 30 in the shield wall form slightly flexible tab-like members 32 at the rear end of the shield. As seen best in FIG. 4, a plurality of lug members or protrusions 34 extend radially inwardly from each of the tabs 32, and also extend circumferentially along each tab 32. Lug members 34 are adapted to fit within and lockingly engage circumferential grooves 36 and 38 of inner tube 10. The flexibility of tab 32 and their corresponding lug members 34 provide advantages in assembling the shielded medical device, and in moving the shield 12 from its unshielded (open) to its shielded (closed) position. The precise size and shape of lug members 34 may be changed to suit the particular situation.

Turning to FIGS. 5a and 5b, a safety-needled syringe embodiment is shown, with like numbers indicating like parts. In FIG. 5a, the outer shield 12 is in its retracted position relative to the inner syringe tube 10 such that needle 16 is unshielded. Ratchet means 14 of the syringe tube 10, and locking nozzle 26 of the outer shield 12 are engaged to prevent rotation of the shield relative to the inner syringe tube 10, while lug member 34 of tabs 32 are seated in circumferential groove 36. As shown in FIGS. 5a and 5b, the inside of inner syringe tube 10 as arranged to be generally cylindrical in shape, and at its forward end is shaped to accommodate the typically rubber end of a standard plunger 20. Thus, chamber 22 of the syringe tube 10 is shown accepting plunger 20 which will either force the contents of chamber 22 through a small annular opening 58a in the ratchet assembly 14 and into and through the needle 16, or aspirate a fluid through the needle 16, the small annular opening 58a in the ratchet assembly, and into the chamber 22. As seen in both FIGS. 5a and 5b, graduated markings 40 typically in cc measurements are placed on shield 12 for clear visibility, although since shield 12 is preferably transparent, the markings 40 may be placed on the syringe tube 10.

After injection, the rubber end of plunger 20 is seated at the accommodating front end of the chamber 22. By applying some force to the shield 12, shield 12 is moved to the position indicated in FIG. 5b such that lugs 34 are seated in circumferential groove 38, and the needle 16 is shielded by shield 12. Shoulder 46 and ledge 50 of the syringe tube 10 keep the lugs 34 of shield 12 firmly in place so that shield 12 cannot accidently retract or fall off of the syringe tube 10 and thereby reexpose the contaminated needle. It is of note with respect to FIGS. 5a and 5b, that the front end of the shield 12 extends further than is shown in FIG. 1 so that the ratchet means 26 of the shield 12 can properly engage ratchet means 14 of the syringe tube 10. Thus, while the shield 12 is essentially identical for all of the medical devices of the invention, its exact length and shape at the front end is dependent on the device with which it is to engage so as to prevent rotation.

Turning to FIGS. 6-8, the inner tube 10 of a blood collection tube holder embodiment is provided. As is seen in FIG. 7, ratchet assembly 14 has an annular opening 58b at the center thereof. Also, as seen in FIG. 6, the ratchet 14 assembly of inner tube 10 of the blood collection tube holder has a cylindrical forwardly extending wall 60 which is provided at the inside circumference thereof with threads 62 or other means by which a standard hollow needle may be attached and communicate through annular opening 58b with cavity 22. For the blood collection tube holder device, inner tube 10 is also provided with a rearwardly extending cylindrical wall 64 may be shaped to receive the forward end of a vacuum blood collection vial (not shown) in sealing engagement therebetween. It should be appreciated that in the phlebotomy embodiment, the flange 28 on the outer shield 12 not only provides a safety ridge for grasping and pushing shield 12, but may be used as a vacuum vial penetration indicator line. Thus, the self-sealing rubber end of the vacuum vial may be axially inserted up until that point without the back point of the standard phlebotomy needle puncturing the same.

As aforementioned, the ratchet assembly 14 of the inner tube 10 includes a plurality of raised teeth 66, which as seen in FIGS. 7 and 8 extend outwardly from the outside surface of wall 60 of rachet assembly 14. Five teeth 66 are shown on diametrically opposed sides of wall 60, but the exact number and exact location of the teeth 66 may be varied. The teeth 66, as was afore-described, mesh with notches 76 of in the locking nozzle 26 of shield 12 to prevent rotation of shield 12 relative to inner tube 10 when the shield is in its retracted position.

The inner tube 110 of the prefilled safety syringe embodiment of the invention is seen in FIG. 9a, with the disposable plunger arm 105 seen in FIG. 9b. (In this embodiment corresponding elements will have corresponding numbers with the numbers of FIG. 9a being greater by one hundred). The inner tube 110 of FIG. 9a combines many of the standard features of a prefilled syringe with the afore-described inner tube features of the instant safety-needled invention. Thus, for purposes of the standard prefilled syringe, the inner tube 110 is preferably made of or lined with glass. The medicated liquid 121 is maintained in chamber 122 which is bounded by the cylindrical wall 142, a shaped metal cap 145 having an hermetic seal 147, and a rubber plunger seal 149 having a male threaded member 151 extending therefrom. Also, for purposes of the standard prefilled syringe, the rear end of the inner tube 110 is provided with a groove 161 for a preferably plastic snap-on flange 163, while the front end metal cap 145 is arranged to mate with a needle hub 165 having a ridge ring 167 on one end for mating with the metal cap 145, and means for accepting and holding a double pointed needle 116 on the other end. Typically, the needle 116 is provided with a protective cover 118 which must be removed before an injection. A disposable plunger arm 105 seen in FIG. 9b is provided with a female thread member 181 which is screwed onto the male threaded member 151 of the inner tube 110 prior to injection. After mating, force may be applied to the plunger arm 105 so as to force the medicated liquid out through the double pointed needle 116.

As seen in FIG. 9a, the inner tube 110 also includes the safety-needled features. Thus, provided in the outer surface of the inner tube 110 are front and rear grooves 138 and 136 into which the lugs of an outer shield may extend, with front groove 138 being deeper than rear groove 136. Also, preferably, the outer surface of inner tube 110 is provided with a shoulder 146 which prevents the outer shield from leaving the front groove 138, as well as a ramped surface 152 which helps provide the clicking/locking action.

Upon assembly of any of the shielded medical devices, preferably by machine in an automated production, the open end of the outer shield 12 is forced over the shoulder 46 (146) of the inner tube 10 (110), (FIG. 9 numbers not being listed hereafter). The lug members 34 attached to tabs 32 initially contact the sloped wall portion 90 (FIG. 1) and the wall portion 90 forces the flexible tabs 32 outwardly in a fanlike manner. As the lug members 34 pass over and by raised shoulder 46, they instantaneously remain spread, both due to the contraction time required to reassume an unstressed position and due to the position assumed with the tabs angling away from wall 42 of tube 10, such that they can be quickly moved past groove 38 without falling into groove 38. As the shield 12 is pushed rearwardly over the inner tube 10, the lug members 34 press against ramp 52 which is of decreasing diameter, i.e., the tabs 32 are no longer flexed outwardly as a result of the reduced diameter of wall 42, and become parallel. The lug members 34 at the end of the shield 12 ultimately pass over slightly raised shoulder 54, and lug members 34 fall into circumferential groove 36, where the shield 12 is substantially fixed as shown in FIG. 5a.

After the medical device is used and becomes contaminated, the user removes the needle from the patient or other contaminated area and presses forward on safety ridge 28. Because circumferential groove 36 is not as deep as circumferential groove 38, lug members 34 are not deeply seated in circumferential groove 36. Since tabs 32 are slightly flexible, it does not take a great deal of force to push the lugs 34 out of groove 36 and over raised shoulder 54. As the shield 12 is pushed forward, the lug members 34 contact ramp 52 in a direction in which the diameter of the wall 42 is increasing. This provides increased friction and tension on the tabs 32, i.e., the user is aware of the increase in force needed to keep the shield 12 moving forward. The lug members 34 eventually fall into circumferential groove 38 with an audible click, providing a positive indication of locking beyond the visual indication. Because of its depth and because of the increased diameter of raised shoulder 46, groove 38 retains the shield fixed as shown in FIG. 5b. It is difficult to remove the shield once it is locked into circumferential groove 38, and a positive lock is assured, completely protecting medical personnel and others against needlestick injuries from the contaminated needle 16. The shielded medical device is then safely discarded in accord with established procedures.

The shielded safety medical devices of FIGS. 1-9 may be used in numerous circumstances and for differing purposes. A common use would be by a phlebotomist (clinician) for obtaining blood samples from a patient. For this usage the phlebotomist (clinician) screws a capped sterile blood collection needle 16 into the threads 62 of inner tube 10. Typically, the phlebotomy needle (not shown) extends a short distance into cavity 22 of the inner tube 10, and a vacuum vial (not shown) having a rubber or plastic stopper is inserted into the tube 10 rather than a plunger. The stopper of the vacuum vial is penetrated by contact with the rearward extension of the needle, and blood is drawn into the vacuum vial through the needle which has been inserted into a vein of the patient. Once the blood sample is taken (if desired, several tubes of blood may be obtained), the needle is removed from the patient, the vacuum vial(s) now filled with a blood sample(s) is removed from the inner tube 10, and the phlebotomist (clinician) then slides the shield 12 over the inner tube 10 until the shield clicks and locks in place, thereby protecting personnel from injury from the contaminated needle or blood. The shielded blood collection tube holder is then safely disposed of, protecting against potential injuries and inadvertent contamination.

When used simply as a syringe, the clinician attaches the appropriate size needle to the syringe tube, removes the end cap and aspirates the required drug, medication, or blood into the syringe. The drug, medication, or other liquid is then administered to the patient directly by injection or through I.V. administration lines. Upon removing the needle from the patient, the safety shield is moved forward until the lugs of the tabs of the outer shield click and lock securely in the forward groove in the syringe tube. With such a procedure, the shield surrounds the needle as shown in FIG. 5b, and the syringe and contaminated needle may then be safely discarded.

Similar procedures are followed with safety syringes with needles already attached, or with pre-filled syringes which ordinarily require loading the syringe into a plunger mechanism in order to administer the drugs, medications, or other fluids contained therein. In either case, the described syringe tube and shield are useful. It is also intended to use a similar shield and inner tube with intravenous catheters.

Turning to FIGS. 10-12, various embodiments of improvements in the groove and protrusion locking arrangement of FIGS. 1-9 are seen. In FIG. 10, improvements are seen in both the protrusion arrangement of the shield and the front groove arrangement of the tube of FIG. 1 (like numerals indicating like parts). In particular, with reference to the shield, shield 12 is seen to have two inwardly extending circumferential protrusions or lugs 34a and 34b. Protrusion 34a is a single continuous "lug" around the inner circumference of the shield 12 and is located forward of, and in relatively close proximity to protrusion 34b. Protrusion 34b, as seen in FIG. 10, is comprised of several lugs 34b. However, unlike the arrangement of FIG. 1, the lugs 34b of FIG. 10 are "connected" by section 234b which is part of the cylindrical wall 70 of the shield 12 rather than being separated by a slot (30) in the shield 12. As will be described hereinafter, the flexibility of the materials used permits the shield 12 to be formed without slots, provided inner tube 10 is arranged with a shoulder 46 over which the protrusions 34a and 34b must slide during assembly.

As seen in FIG. 10, inner tube 10 is also altered in comparison to FIG. 1. In particular, two forward grooves 38a and 38b are provided into which protrusions (lugs) 34a and 34b may lock. Preferably, groove 38b having front ledge 48b and rear ledge 50b is located near the beginning of the ramp 52 (i.e. at the end having the smallest diameter) on the outer surface of tube 10, while groove 38a having front ledge 48a and rear ledge 50a is located adjacent shoulder 46 and in relatively close proximity to groove 38b. In the preferred embodiment, groove 38a is of a slightly greater width than groove 38b1, while protrusion 34a has a slightly greater width than protrusion 34b (and groove 38b). In this summer, during the shielding action when protrusions 34b of shield 12 are unseated from rear groove 36 (seen in FIGS. 1 and 5), and the shield is moved forward, protrusion 34a will not engage in groove 38b. Rather, as seen in FIG. 11a, protrusion 34a engages groove 38a, while protrusion 34b engages groove 38b. This double lock serves several purposes. First, the double lock provides additional stability to the apparatus in the shielded position such that even large axial or torque forces will not cause the shield and tube to disengage. This stability is at least partially due to the fact that the shield 12 and tube 10 are engaged in two axial positions which doubles frictional forces and prevents rotation about a single plane. Second, the double lock prevents the shield from sliding back into the retracted (unshielded) position. Finally, the double lock provides an added measure of security in that should the first protrusion 34a disengage from the forward groove 38a with the shield moving in the forward direction, the second protrusion 34b will lock into forward groove 38a thereby continuing the protection against needlesticks by the contaminated needle.

Turning to FIG. 12A, a second embodiment of the shield 12 shown in FIG. 10 are provided. FIG. 12A shows inwardly extending circumferential protrusions (lugs) 34a and 34b which are both continuous (i.e. uninterrupted). The shield 12 of FIG. 12A is also shown in FIG. 11B in its shielded (i.e. engaged) position with reference to inner tube 10 which is intended to be the equivalent of any of the inner tubes shown in FIGS. 1, 5A, 5B, 6, or 9. With a double protrusion arrangement 34a, 34b on the shield 12 and a single forward groove 38 in the inner tube 10, in the shielded position, the forward protrusion 34a engages groove 38, while the rear protrusion 34b engages the ramp 52 and/or outer circumference 20 of the inner tube 10. This arrangement provides excellent stability against large axial and/or torque forces applied to the shield relative to the inner tube, and also further provides the added measure of security where lug 34b can still engage groove 38 after lug 34a has been dislodged.

Turning to FIGS. 12B and 12C, additional embodiments of the outer shield 12 are provided. In FIG. 12B, the forward protrusion 34a is shown as being interrupted, with section 234a of wall 70 being seen therebetween. Protrusion 34b, on the other hand is uninterrupted. In FIG. 12C, both forward protrusion 34a and rear protrusion 34b are shown being interrupted. If desired (as shown in phantom), slots 30 in wall 70 may be provided to cause the interruption of one or both of the protrusions. Thus, it will be appreciated that various combinations of interrupted and uninterrupted protrusions with or without slots, along with one or two forward inner tube grooves can be made within the scope of the invention.

Because shields without slots are shown in FIGS. 10, 11A, 11B, and 12A and 12B, it will be appreciated that the material of the shields must be flexible enough to permit the shield to extend over shoulder 46 of inner tube 12 so as to permit lugs 34a and 34b to pass over groove 38 (or grooves 38a and 38b) during assembly of the medical devices. Thus, in the preferred embodiment, a polypropylene or polyethylene plastic having a thickness of 0.032±0.001 inches is utilized for the shield. The following preferred dimensions (in inches) are believed to function well in both assembly and usage:

Wall (70) thickness of outer shield (12)=0.032±0.001
Inner diameter of the outer shield (12)=0.816±0.002
Outer shield (12) protrusion (34) height=0.018
Diameter of front shoulder (46) of inner tube (10)=0.810±0.001
Back ledge (50 or 50a) diameter of inner tube (10)=0.806±0.002
Midpoint along length of tube (10) outer diameter=0.780±0.002
Front groove (38 or 38a) depth from shoulder (46)=0.015
Front groove (38 or 38a) width=0.070±0.002
Width of protrusion (34)=0.063±0.003
Distance between back ledge (50a) of forward front groove and front ledge (48b) of rear front groove=0.125

Of course, while these are preferred dimensions, wide latitude in dimensions is contemplated, and many other dimensions would be suitable. The width dimension of the second protrusion (34b) and the second front groove (38b) have not been set forth, as they could be the same as the first protrusion (34a) and the first front groove (38a), or they could be arranged such that the width of groove 38b (and hence protrusion 34b) is smaller than the width of protrusion 34a as suggested above. Regardless, with the provided diameter dimensions, protrusions 34 of the shield will pass over the inner tube without stress as the inner diameter of the outer shield at the protrusions and the outer diameter of the non-ramped section of the inner tube are the same. Movement of the protrusions 34 along ramp 52 (or 54) during use will cause additional friction as the shield must be stressed in expansion. The movement of protrusions 34 into their respective grooves will therefore preferably provide an audible click as the shield reassumes its unstressed position.

There has been described and illustrated herein various improved shielded safety medical devices. While particular embodiments of the invention have been described, it is not intended that the invention be limited thereby, as it is intended that the invention be broad in scope. Thus, for example, while the shield of the invention was described as having "protrusions" or "lugs", the terminology is intended to be broad so as to encompass any inward extension which will mate with the inner tube "groove". Further, while the two protrusion embodiments of the inner tube were described as having two protrusions in relatively close proximity at the forward end, those skilled in the art will appreciate that the exact location is not critical provided the contaminated needle is shielded by the shield after use and additional stability is provided. In fact, the invention is intended to encompass single protrusion embodiments as seen in FIGS. 13a and 13b where no slits are provided in the rear of the outer shield. Indeed, as seen in FIGS. 13a and 13b, the protrusion 34 can be placed in different locations, and may be interrupted (as seen in phantom) or not. Further yet, it should be recognized that while embodiments having two and three grooves were disclosed, four or more grooves could be utilized. Likewise, while the inner tube was described as having a substantially cylindrical shape with conical ramps formed on either end, it will be appreciated that the entire outer surface of the inner tube could be ramped. Therefore, it will be apparent to those skilled in the art that yet other changes and modifications may be made to the invention as described without departing from the scope of the invention as so claimed.

I claim:

1. A medical device for assembly with a hollow needle, comprising:
    (a) an inner tube member having a substantially cylindrical inner surface, a front end adapted to have said hollow needle secured thereto, an open rear end, an outer surface having first and second circumferential grooves, said first groove being rearward of said second groove, said outer surface further including a shoulder forward of said second groove with said shoulder having an outer diameter greater than said outer surface rearward of said second groove; and
    (b) a hollow outer shield member having a substantially cylindrical inner surface with an inner diameter slightly larger than an outer diameter of said outer surface of said inner tube, a front end and a rear end each having an opening therein, at least one protrusion extending inwardly from said inner surface of said outer shield, said at least one protrusion being adapted to engage said first circumferential groove to maintain said shield member in a first retracted position in which said hollow needle is exposed, and further adapted to fixedly engage said second circumferential groove to maintain said shield member in a second extended position in which said needle is covered by said shield,
    wherein said protrusion is disengageable from said first circumferential groove and said shield member is slidable between said first position and said second position, and
    wherein said an inner diameter of said at least one protrusion is smaller than said outer diameter of said shoulder and said outer shield member is sufficiently flexible and resilient such that said shield member can be forced over said shoulder in assembling said medical device and substantially reassume its normal diameter when unstressed.

2. A medical device according to claim 1, wherein:
    said outer surface of said inner tube member is arranged to be larger in diameter at a rearward end of said second circumferential groove than at a position forward of said first circumferential groove, such that at least a portion of said outer surface comprises a cylindrical ramp, and said protrusion is arranged to slidably engage said outer surface of said tube member such that when engaging said cylindrical ramp in moving from said first position to said second position, additional tension is placed on said protrusion and additional resistance to movement is obtained.

3. A medical device according to claim 2, wherein:

said outer shield and said inner tube are of nearly equal length, and along most of its length, said outer surface of said shield member is generally cylindrical;

said outer surface of said shield member further includes at its forward end a generally conical section terminating at said generally cylindrical outer shield member surface in a flanged safety ridge; and said first groove is located substantially at said rear end of said inner tube, and said second groove is located substantially at the front end of said inner tube.

4. A medical device according to claim 3, wherein:

said at least one protrusion extends intact circumferentially around said inner surface of said shield member.

5. A medical device according to claim 1, wherein:

said outer shield further comprises two inwardly extending protrusions which are spaced axially along a longitudinal axis of said outer shield, wherein a first of said protrusions is arranged to engage said first groove in said retracted position and a second of said protrusions is arranged to engage said second groove in said extended position.

6. A medical device according to claim 5, wherein:

a distance between said first and second protrusions is substantially smaller relative to a second distance between said first and second grooves.

7. A medical device according to claim 6, wherein:

at least one of said first and second protrusions is interrupted to form a plurality of circumferentially spaced inwardly extending lugs.

8. A medical device according to claim 6, wherein:

said inner tube further comprises a third groove wherein a third distance between said second and third grooves is substantially equal to said distance between said first and second protrusions.

9. A medical device according to claim 8, wherein:

a thickness of said third groove taken along said longitudinal axis is smaller than a second thickness of at least one of said first and second protrusions taken along said longitudinal axis.

10. A medical device according to claim 8, wherein:

at least one of said first and second protrusions is interrupted to form a plurality of circumferentially spaced inwardly extending lugs.

11. A medical device according to claim 8, wherein:

said shield member further includes a plurality of slits in said rear end of said shield member, said slits interrupting at least one of said first and second protrusions.

12. A medical device according to claim 5, wherein:

said tube member is arranged to receive a plunger means for helping aspirate fluid though said hollow needle and into said inner tube member and for injecting said fluid out through said inner tube member and said hollow needle.

13. A medical device according to claim 5, wherein: said tube member is arranged to receive a vacuum blood collection vial which may be pierced by said hollow needle inside said tube member for collecting a blood sample.

14. A medical device for assembly with a hollow needle, comprising:

(a) an inner tube member having a substantially cylindrical inner surface, a front end adapted to have said hollow needle secured thereto, an open rear end, and an outer surface having first and second circumferential grooves, said first groove being rearward of said second groove; and (b) a hollow outer shield member having a substantially cylindrical inner surface with an inner diameter slightly larger than an outer diameter of said outer surface of said inner tube, a front end and a rear end each having an opening therein, at least a first and a second protrusion extending inwardly from said inner surface of said outer shield and axially spaced along a longitudinal axis of said outer shield, said first protrusion being adapted to engage said first circumferential groove to maintain said shield member in a first retracted position in which said hollow needle is exposed, and said second protrusion being adapted to fixedly engage said second circumferential groove to maintain said shield member in a second extended position in which said needle is covered by said shield, wherein said first portrusion is disengageable from said first circumferential groove and said shield member is slidable between said first position and said second position.

15. A medical device according to claim 14, wherein:

said first protrusion is adapted to engage an outer surface of said outer shield when said second protrusion engages said second circumferential groove in said second position.

16. A medical device according to claim 15, wherein:

said first protrusion is adapted to engage said second circumferential groove should said second protrusion disengage from said second circumferential groove.

17. A medical device according to claim 14, wherein:

said outer surface of said inner tube includes a shoulder forward of said second groove with said shoulder having an outer diameter greater than said outer surface rearward of said second groove, said outer surface of said inner tube member is arranged to be larger in diameter at a rearward end of said second circumferential groove than at a position forward of said first circumferential groove, such that at least a portion of said outer surface comprises a cylindrical ramp, and said first and second protrusions are arranged to slidably engage said outer surface of said tube manner such that when engaging said cylindrical in moving from said first position to said second position, additional tension is placed on said protrusions and additional resistance to movement is obtained, and wherein when said shield member is in said second position with said second protrusion engaging said second groove, said first protrusion is arranged to engage said ramp.

18. A medical device according to claim 17, wherein:

at least one of said first and second protrusions is interrupted to form a plurality of circumferentially spaced inwardly extending lugs.

19. A medical device according to claim 14, wherein:

said inner tube further comprises a third groove axially spaced from said second groove such that a distance between said second and third grooves is substantially equal to a second distance between said first and second protrusions, and when said outer shield is in said second position, said first protrusion engages said third groove.

20. A medical device according to claim 1, wherein:

said inner tube member further comprises a front end wall and a hollow neck portion supported by said front end wall, said hollow neck portion extending at least a short distance forward of said front end wall and having an opening adjacent said annular opening, said neck portion including outwardly extending locking means about an outer surface of said hollow neck portion, and said shield member further comprises a front end wall of said shield member and a circular nozzle supported by said front end wall of said shield member, said circular nozzle and shield member front end wall having opening for permitting the hollow needle to pass therethrough, and said circular nozzle having inwardly extending locking means located about the inner surface of said circular nozzle and adapted to lock with said outwardly extending locking means to prevent rotational motion of said shield member relative to said tube member when said shield member is in said retracted position.

21. A medical device according to claim 20, wherein:

said outwardly extending locking means comprises a plurality of radially extending ratchet teeth; and said inwardly extending locking means comprises a nozzle having a plurality of notches for meshing with at least said teeth to prevent rotation of said outer shield relative to said inner tube.

22. A medical device according to claim 1, wherein:

said outer surface of said inner tube is arranged with a first ramp substantially forwardly adjacent said first circumferential groove, said first ramp being of decreasing diameter as it extends forward of said first circumferential groove, and said outer surface of said inner tube is further arranged with a second ramp substantially rearwardly adjacent of said first circumferential groove, said second ramp being of increasing diameter as it extends forward toward said second circumferential groove, wherein said at least one protrusion is arranged to slidably engage said outer surface of said inner tube member such that when engaging said first ramp and said second ramp in moving from said first position to said second position, tension on said at least one protrusion first decreases and then increases.

23. A medical device according to claim 22, wherein:

said outer shield and said inner tube are of nearly equal length, and said outer surface of said shield member is generally cylindrical and of substantially constant diameter between said first and second ramps; and said first groove is located substantially at said rear end of said inner tube, and said second groove is located substantially at the front end of said inner tube.

* * * * *